US008888767B2

(12) United States Patent
Neuberger et al.

(10) Patent No.: US 8,888,767 B2
(45) Date of Patent: Nov. 18, 2014

(54) DIODE LASER INDUCED VAPOR/PLASMA MEDIATED MEDICAL PROCEDURES AND DEVICE

(75) Inventors: Wolfgang Neuberger, F.T. Labuan (MY); Walter Cecchetti, Saonara (IT)

(73) Assignee: Biolitec Pharma Marketing Ltd, F. T. Labuan (MY)

( * ) Notice: Subject to any disclaimer, the term of this patent is extended or adjusted under 35 U.S.C. 154(b) by 176 days.

(21) Appl. No.: 12/629,313

(22) Filed: Dec. 2, 2009

(65) Prior Publication Data

US 2011/0224660 A1    Sep. 15, 2011

Related U.S. Application Data

(60) Provisional application No. 61/119,259, filed on Dec. 2, 2008.

(51) Int. Cl.

| A61B 18/22 | (2006.01) |
| A61B 18/04 | (2006.01) |
| A61B 18/26 | (2006.01) |
| A61N 1/44 | (2006.01) |

(52) U.S. Cl.
CPC ............... *A61B 18/22* (2013.01); *A61B 18/042* (2013.01); *A61B 2018/263* (2013.01); *A61N 1/44* (2013.01)
USPC .................... 606/15; 606/16; 606/2.5; 606/3; 606/7

(58) Field of Classification Search
USPC ....................... 606/15, 16, 2.5, 3, 7
See application file for complete search history.

(56) References Cited

U.S. PATENT DOCUMENTS

| 4,917,084 A | * | 4/1990 | Sinofsky ............................ 606/7 |
| 5,409,483 A | * | 4/1995 | Campbell et al. ............... 606/15 |
| 6,315,772 B1 | * | 11/2001 | Marchitto et al. ................ 606/9 |
| 2004/0057471 A1 | * | 3/2004 | Shevy et al. ...................... 372/6 |
| 2005/0021013 A1 | * | 1/2005 | Visuri et al. .................... 606/15 |
| 2007/0055220 A1 | * | 3/2007 | Lin et al. ............................ 606/5 |
| 2007/0219601 A1 | * | 9/2007 | Neuberger ...................... 607/89 |

* cited by examiner

*Primary Examiner* — Yuanda Zhang
*Assistant Examiner* — Michael Carter
(74) *Attorney, Agent, or Firm* — Bolesh J. Skutnik; BJ Associates

(57) ABSTRACT

An improved method and device for safe and efficient medical applications is provided. In a preferred embodiment, based on using the inherent benefits of laser diodes (such as efficient power generation from a reliable and compact solid state device), plasmas and high energy vapors are produced for medical applications with power levels and power densities sufficient to treat medical indications and avoid the creation of extensive damage zones. Transmissions means in different configurations are used to achieve a high power density, which is able to initiate plasma and high-energy vapor at the tip. Once a sparkless plasma and high energy vapor bubbles are formed, it is often found that it will also absorb other wavelengths in addition to the one that initiated it. As a consequence, other wavelengths more efficiently generated by diodes or diode pumped lasers may be added into the beam in order to improve treatment efficiency. For example, the 1470 nm wavelength can be used to produces sparkler-less plasma bubbles, together with the 980 nm wavelength to produce tissue vaporization and an excellent haemostasis effect. Once plasma and or high-energy vapors are in place, radiation from this zone determine tissue effects. In another embodiment, high peak power pulsed radiation is used. Wavelengths of 1470 nm, 1940 nm, or 1550 nm are preferred. Additionally it can be applied in combination with another wavelength with medium absorption in water such as 980 nm. In another embodiment a concentric double core fiber is used, in which the ignition radiation is guided in near single mode, inner core and the radiation used to maintain and enhance the pulse is guided into the surrounding second outer core.

20 Claims, 4 Drawing Sheets

DIODE LASER INDUCED VAPOR/PLASMA MEDIATED MEDICAL PROCEDURES AND DEVICE

DOMESTIC PRIORITY UNDER 35 USC 119(e)

This application claims the benefit and priority of U.S. Provisional Application Ser. No. 61/119,259 filed Dec. 2, 2008, entitled "Diode Laser Induced Vapor/Plasma Mediated Medical Procedures and Device" by Wolfgang Neuberger and Walter Cecchetti, which is incorporated by reference herein.

BACKGROUND OF THE INVENTION

1. Field of the Invention

The present invention is related to minimally invasive devices and methods for treatment of biological tissue. More particularly, the invention relates to medical procedures mediated by diode laser induced vapor/plasma in order to achieve specific effects on tissues.

2. State of the Art Statement

Since laser technology was introduced in markets for medical procedures, numerous laser devices have been proposed for tissue removal. Laser energy can be used taking advantage of its different advantageous features. As a consequence, tissue can be vaporized, liquefied, coagulated, etc., through laser radiation by means of using different treatment parameters, such as energy, power, wavelength, etc.

Laser energy can also lead to plasma formation, by means of using appropriate radiation parameters and environment properties. Plasma formation is achieved through optical breakdown, which is a non linear effect produced when laser radiation is sufficiently condensed in time and space, leading to high density power. During optical breakdown of electromagnetic energy, an ionized state or plasma is formed. Plasma expands rapidly generating a shockwave which may be followed by cavitation or vapor bubble formation. Cavitation or vapor bubble collapse further contributes to shockwave generation. As a consequence, by focusing laser energy on a target material such as a gas, liquid or solid, the latter may be damaged by the sequence of optical breakdown, plasma formation and shockwave generation. Plasma and cavitation phenomena are both associated with strong photo and thermo-ablative effects. Inside plasma bubbles, high temperatures of over a thousand degrees arise. The presence of cavitation effects is always associated with a typical crackling noise produced by the shockwaves. One example of how this can be achieved is by providing an initial pulse as for instance in the FREDDY device (in this case generated by a flash lamp pumped frequency doubled pulsed YAG laser). The plasma produced by FREDDY laser is a sparkling plasma.

According to the afore-mentioned mechanism of action, laser energy can be applied in two different ways to achieve tissue removal (by means of plasma formation). Indirectly, by focusing it upon a target placed between laser beam and tissue, which in turn vibrates due to optical breakdown and emulsifies tissue, or directly on target tissue in order to achieve its removal.

In the first case, laser energy is transmitted through an optical fiber generating a shockwave which produces vibrational motion in the target (placed at a handpiece's tip) that is then transmitted to the tissue in order to cause emulsification.

In U.S. Pat. No. 5,224,942, Beuchat et al. disclose a method and apparatus using laser energy for destroying body tissue which includes a handpiece comprising a surgical tip assembly which is driven by means of laser to achieve optical breakdown, plasma formation and shockwave generation to emulsify or destroy body tissue. As laser is focused on a target (placed inside the handpiece) which vibrates due to plasma formation, mild energy is applied to tissue, which is only emulsified by mechanical vibration of handpiece tip. As a consequence, versatility of this system is limited as it is aimed at treating soft tissue.

U.S. Pat. No. 5,324,282 by Dodick et al., teaches a system based on similar principles. Pulsed laser energy is discharged to strike a metal target, which acts as a transducer converting the electromagnetic energy to shockwaves that are directed to tissue to be treated. The mechanical shockwaves cause the tissue to fracture.

In U.S. Patent Application No. 2004/0167504, Thyzel et al. disclose a surgical needle for fracturing tissue comprising a distal operating port which holds tissue. Pulsed laser energy is applied to a target through an optical fiber, generating shockwaves due to plasma formation from the optical breakdown of target, impinging on the tissue to be fractured. This patent is mainly focused on fracturing tissue, so here again system versatility is limited.

Afore-mentioned patents are founded on plasma formation upon a target material, which converts optical breakdown into mechanical vibrations. As a consequence, energy loss occurs in this transduction, diminishing treatment efficacy. Furthermore, mechanical vibrations are not selective with the tissue to be treated, so effects on other tissue rather than tissue to be treated may appear. In other words, not only desired tissue may be affected by vibrations.

When laser radiation is directly focused on tissue in order to achieve its removal, target for radiation is now tissue itself. Usually, tissue to be removed is surrounded by liquid and illuminated with laser radiation above a threshold intensity level, generating a shockwave. Thus, tissue is damaged by mechanical energy, rather than melting. This method is widely used in order to break calculi, stones, and calcified tissue within the body. For instance, plasma has been used in medical treatments in the form of ionized Argon gas for the ablation of mucosal layers. This way stones have been fractured by the shockwaves created due to the collapse of bubbles initiated by plasma formation at the tip of fiber optics delivering laser pulses from flash lamp pumped, frequency doubled YAG lasers (FREDDY).

In U.S. Pat. No. 5,071,422, Watson et al. disclose a method for breaking down material within the body, based on a pulsed dye laser source. Optical fiber is inserted in the area to be treated, which is surrounded with liquid and then radiated with pulsed dye laser energy in order to achieve fragmentation by means of shockwaves. This invention basically discloses calculi and stone fragmentation. But if dye laser radiation is not absorbed by stones, plasma formation will not occur and laser lithotripsy will not be effective. The plasma produced by a dye laser is sparkling plasma. Furthermore, as a pulsed dye laser source is used, frequent maintenance may be required as this source is not a solid-state laser.

U.S. Pat. No. 5,963,575 by Müller et al., discloses a Q-switched laser system for laser lithotripsy. The system incorporates longer pulse duration, increasing plasma formation and consequently shockwave production. Laser source is preferably a Nd:YAG laser, which is a ionic crystal source. As a consequence, it has low efficiency, large dimensions, and needs liquid cooling. Moreover, it requires alignment, as laser radiation is conveyed to the treatment zone by means of mirrors instead of optical fibers. Furthermore, this technology lacks precision compared to other laser technologies.

In U.S. Pat. No. 4,960,108, Reichel et al. teach a laser-induced lithotripter in which pulsed laser radiation in the vicinity of infrared region is concentrated at a concrement to be destroyed which is surrounded with an aqueous rinsing liquid. Concrement is destroyed by breakdown (plasma) of rinsing liquid, giving rise to shockwave and cavitation. Rinsing liquid includes a metal compound which lowers the energy required for said breakdown.

All previous-mentioned patents only disclose use of laser sources that may be usually voluminous, inaccurate, inefficient and/or requiring frequent maintenance.

Due to the disadvantages and lack of versatility of current plasma formation techniques, a need exists for a device that provides a fast and safe alternative to address their shortcomings.

OBJECTIVES AND BRIEF SUMMARY OF THE INVENTION

It is an objective of the present invention to provide a device to generate plasma and vapors for medical applications by means of laser diodes using power levels and power densities sufficient to treat various medical indications and avoid creating extensive damage zones.

It is also an objective of the present invention to provide a device which utilizes advantageous features of diode laser to generate plasma and vapors for medical applications, leading to more efficient and safer treatments.

It is another objective of the present invention to provide a system to generate plasma and vapors for medical applications by means of laser diodes which enhances versatility of treatments that can be carried out.

It is yet another objective of the present invention to provide a method to generate a sparkless-plasma and vapors for medical applications by means of laser diodes using power levels and power densities sufficient to treat medical indications and avoid creating extensive damage zones.

Briefly stated, the present invention provides an improved method and device for safe and efficient medical applications. In a preferred embodiment, based on using the inherent benefits of laser diodes (such as efficient power generation from a reliable and compact solid state device), plasmas and high energy vapors are produced for medical applications with power levels and power densities sufficient to treat medical indications and avoid the creation of extensive damage zones. Transmissions means in different configurations are used to achieve a high power density, which is able to initiate plasma and high-energy vapor at the tip. Once a sparkless plasma and high energy vapor bubbles are formed, it is often found that it will also absorb other wavelengths in addition to the one that initiated it. As a consequence, other wavelengths more efficiently generated by diodes or diode pumped lasers may be added into the beam in order to improve treatment efficiency. For example, the 1470 nm wavelength can be used to produces sparkler-less plasma bubbles, together with the 980 nm wavelength to produce tissue vaporization and an excellent haemostasis effect. Once plasma and or high-energy vapors are in place, radiation from this zone determine tissue effects. In another embodiment, high peak power pulsed radiation is used. Wavelengths of 1470 nm, 1940 nm, or 1550 nm are preferred. Additionally it can be applied in combination with another wavelength with medium absorption in water such as 980 nm. In another embodiment a concentric double core fiber is used, in which the ignition radiation is guided in near single mode, inner core and the radiation used to maintain and enhance the pulse is guided into the surrounding second outer core.

The above, and other objects, features and advantages of the present invention will become apparent from the following description read in conjunction with the accompanying drawings.

DETAILED DESCRIPTION OF PREFERRED EMBODIMENTS

Diode lasers have been used in medicine thanks to the favorable laser tissue interaction of the respective wavelength providing absorption and coagulation as well as vaporization. For equal output power, diode lasers are smaller, lighter, air cooled, with high reliability and without alignment and maintenance requirements, especially compared to non-solid state lasers or frequency-doubled solid state lasers.

Some of the before-mentioned techniques limitations and problems can be overcome by using the inherent benefits of laser diodes (such as efficient power generation from a reliable and compact solid state device) in order to generate sparkless plasma and vapors for medical applications with power levels and power densities sufficient to treat medical indications and avoid the creation of extensive damage zones.

As mentioned previously, high power densities are required to initiate plasma/vapor formation and/or a high absorption on the target. However it is possible to use focusing means to initiate plasma/vapor formation as well: an example is the use of a conical fiber tip in an aqueous environment initially submerged; the radiation exits from the front end into the water.

When highly absorbed continuous wave radiation is applied to an aqueous material, water molecules are highly and rapidly heated. This immediate and extremely high heating causes a ionization with rapid expansion, producing a sparkless plasma bubble, which collapses a few millimeters away and after few milliseconds, producing a crackling noise. Successively, after few milliseconds, the process repeats and a crackling noise can be heard, which is produced by the bubbles' growth and collapse. These bubbles reach an interior temperature of over a thousand degrees. As a consequence, they have a considerable thermo-ablative effect and release their thermal energy in the surrounding water. So the hemostatic effect of highly absorbed radiation lasers in tissue treatments is not related to direct laser interaction with the tissue itself. Instead, it occurs due to the thermo spray effect of vapor and hot water generated around plasma bubbles, which releases thermal energy in the water. This is paradigm switch.

Figure 1A:
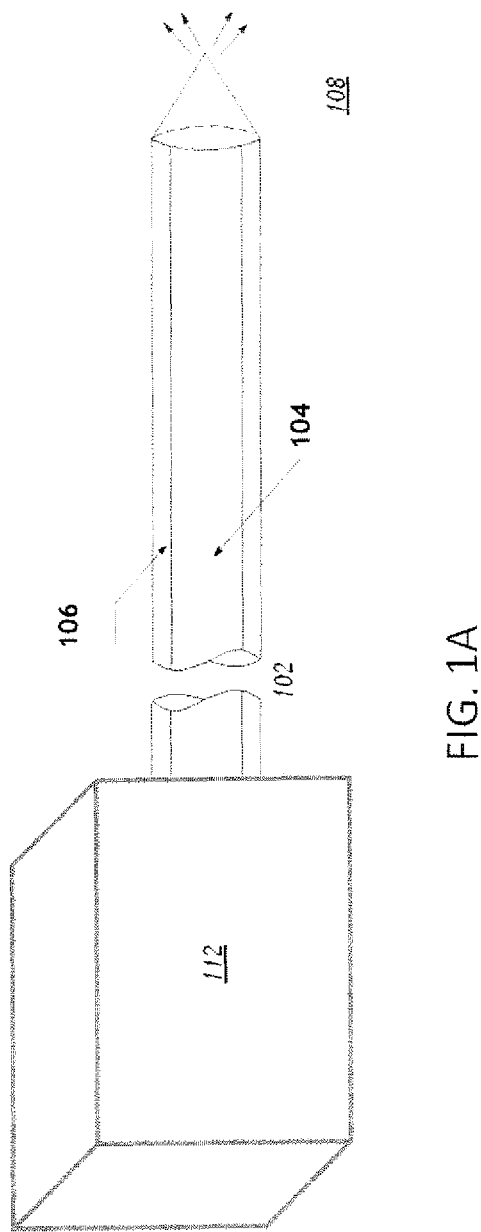
FIGS. 1a and 1b depict a preferred embodiment of the present invention in which a plasma bubble is produced due to laser radiation.
Figure 1B:
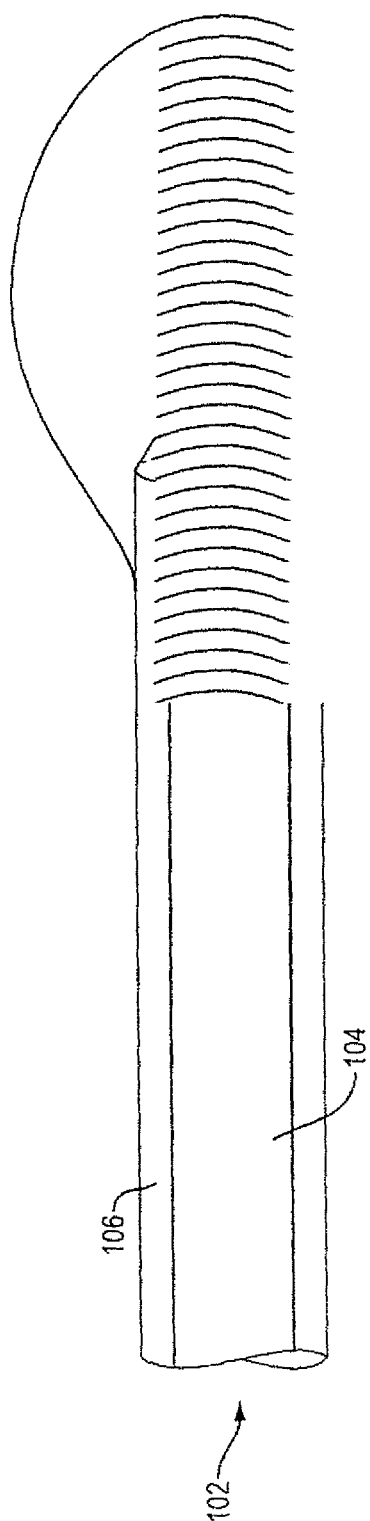

FIGS. 1a and 1b depict a preferred embodiment of the present invention in which optical fiber 102 comprising core 104 and clad 106, is optically coupled to laser light source 112 and emits laser energy to liquid 108 in order to produce plasma formation. Bubble 110 will be formed provided the wavelength and power are adequately chosen in order to create sufficient absorption in the environment. For instance, as 1470±60 nm wavelength is highly absorbed in water, it is appropriate for this purpose when power density is sufficient. Optical fiber 102 tip is preferably conically shaped in order to achieve a greater tissue ablation. The high power density achieved is capable of initiating plasma and high-energy vapor at the tip. It is often found that once formed it will also absorb other wavelengths in addition to the one that initiated it. As a consequence, other wavelengths more efficiently generated by diodes or diode pumped lasers (for instance, 980±60 nm) may be added into the beam in order to improve treatment efficiency. Once plasma and or high-energy vapors are in place radiation from this zone will determine the tissue effects. Since the medium has a very high absorption coefficient of the radiation it can be the mediator of interactions between radiation and tissue. Often, the maximum radiation wavelength emitted by plasma will tend to be in the visible range of the spectrum and due to tissue scattering, higher absorption in the tissue will be observed, compared to conventional infrared diode lasers.

Furthermore, coagulation is generally dependent on the thermo spray of the very hot medium spray, which is produced by the 'plasma' bubbles. It also can be achieved in the tissue due to sufficient penetration of certain parts of the spectrum emitted by the plasma and certain parts of the original laser radiation being transmitted to the tissue as well as the interaction of the high-energy vapors with tissue.

According to afore-mentioned explanation, this invention accomplishes substantial versatility regarding to the variety of medical treatments that can be performed by its means.

As a preferred embodiment, the invention is practiced in tissue containing sufficient quantities of water in or in an aqueous environment provided by saline solution or other biocompatible liquids.

The present invention is further illustrated by the following example, but is not limited thereby.

Example

Multi Wavelength Laser Tissue Resection and Removal

Figure 2:
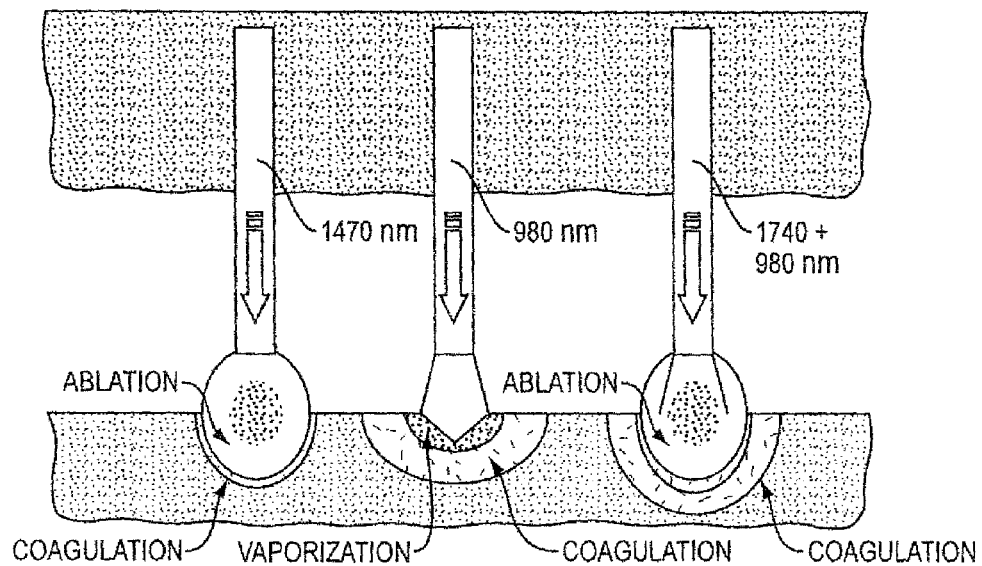
FIG. 2 shows a diagram representing the combined effects obtained on tissues by means of dual wavelength laser radiation.

A multi-diode laser source is able to deliver one or more simultaneous wavelengths in the same optical fiber, for instance 980 nm together with 1470 nm. At 1470 nm there is high absorption in water, thus leading to formation of high energy bubbles at fiber tip (cavitation and/or sparkless plasma effect). This effect is able to produce fast ablation of soft tissue. At 980 nm there is lower absorption in water, but high absorption in blood, thus good hemostatic effect can be achieved. With the multi-diode laser used in BPH treatment, fast ablation on prostatic tissue with a good hemostatic effect can be accomplished. FIG. 2 depicts the effects of combining these two wavelengths for tissue treatment.

The usage of side firing fibers allows for the ablation of prostatic tissue, combined with high depth of hemostasis, during the BPH laser treatment. By using the multi-diode laser with a conical tip fiber, fast ablation of a greater part of prostatic tissue with good hemostasis is accomplished, during BPH laser treatment. Following in vitro and clinical studies, we verified that the 1470 nm diode laser presents an excellent performance regarding effects produced.

Effects produced by the optical fiber immersed in water, and connected to a 1470 nm diode laser source, were verified to have plasma formation thresholds that are very close to those needed for producing similar effects with a 1940 nm diode laser. Furthermore, 1470 nm diode laser produces similar effects in water as thulium laser, and therefore in biological matter. However, diode lasers have many advantages when comparing to ionic crystal lasers such as thulium. For instance, 1470 nm diode laser has an efficiency of 23% whereas thulium laser's efficiency is 6%. In addition, for equal output power, diode lasers are smaller, lighter, air cooled, more reliable and with less alignment and maintenance requirements.

When using a diode laser emitting at 1470 nm in continuous mode, fiber tip immersed in water creates high energy bubbles, which were observed, after investigation, to be a sparkless plasma bubbles. These plasma bubbles present occasional sparks (always present when using Ho:YAG lasers with a pulse duration shorter than 300 μsec), so we call them "sparkler-less" or "sparkless" plasma bubbles. The 1470 nm radiation impinged water molecules in contact with fiber tip, leading to fast heating, with cavitation bubble formation, and thermo spray of boiling hot water. All electromagnetic energy is converted into thermal energy due to the high absorption. Thus, an optical path of 1 mm of water absorbs almost 100% of radiation.

This fast heat-up produces a rapidly growing amount of boiling hot water and creates a sparkler-less plasma bubble and consequently shockwave production. After a few milliseconds, the process occurs again with an associated crepitating noise. The sparkler-less plasma bubbles produce similar effects as sparkling plasma bubbles, with shockwave noise but with lower energy. These bubbles are highly destructive due to thermo ablative effects, and their associated thermal energy affects surrounding water within a radius of few millimeters. Consequently, 1470 nm diode laser also contributes to hemostatic effect, which is not produced by direct interaction of radiation with biological tissue, but is mediated by water. Hemostatic effect is produced by a thermo spray of boiling hot water, created on the fiber tip from the cavitation bubble which, when released, delivers thermal energy to the surrounding water.

Considering the previous paragraphs, plasma bubbles were created, using continuous wave sources, a thermo-ablation effect with high energy was achieved. This is an especially novel conception when compared to prior art, which discloses generally only pulsed laser sources.

Due to the high efficacy of 1470 nm diode laser, a new high power diode laser with a double band of emission was conceived and developed, (the COMBO laser) which combines the thermo-ablative properties of the 1470 nm radiation with the hemostatic properties of radiation at 980 nm.

Therefore, a high power diode laser for BPH treatment was developed, using 1470 nm radiation for a fast ablation of tissue, and 980 nm radiation in order to have good penetration on tissue and obtain a controlled and efficient hemostatic effect, without the need of paying special attention to optical fiber's movement speed. The device was also designed with the possibility to select a single wavelength for performing specific surgical applications.

In order to obtain fast ablation combined with good hemostatic effects, power emitted is referred to as the sum of the powers emitted at both wavelengths, respectively 980 nm and 1470 nm. For example, when using total laser power of 100 W; 70 W comes from the 980 nm source and 30 W comes from the 1470 nm source.

Clinical trials and vitro tests with histological results using a prototype of present invention (the COMBO laser) have proven the efficacy of combining two wavelengths for achieving effective sparkler-less plasma formation for desired tissue effects, particularly 1470±60 nm and 980±60 nm diode lasers. Additionally a 1940±60 nm diode laser, which is even more highly absorbed by water can be used appropriately in combination with either previous wavelength. When the 1470 nm wavelength is delivered by a thin optical fiber immersed in water, it produces sparkler-less plasma bubbles with threshold levels as low as 2 w of emitted power in 600 um fiber. The plasma produced by 1470 nm is capable of producing a fast ablation of soft tissue with thin coagulation as well as rupture of hard tissue. The 980 nm wavelength has excellent absorption in blood and less absorption in water. It can produce tissue vaporization associated with a haemostatic effect with a clear whitening. Penetration on tissue is about 2-3 mm. With the COMBO laser, the 1470 nm wavelength produces a plasma bubble on the fiber tip immersed in water. When a simultaneous emission of 980 nm wavelength in the same fiber, arrives into the plasma bubble, it is absorbed at around 70% and the residual 30% exits plasma bubble. Consequently, 70% of the 980 nm energy is converted into plasma, and 70% of this wavelength works as a pump for the plasma bubble produced by the 1470 nm wavelength. The residual 30%, of the 980 nm, reaches the tissue and can produce further homeostasis. Exemplifying this further, with the COMBO laser emitting at a power of 100 W, 75 W were measured at 980 nm and 29 W were measured at 1470 nm. When 100 W were delivered with the fiber immersed in water, plasma bubbles were generated on fiber tip, and measurements were 16 W at 980 nm residual out of the plasma bubble. The power supply of the plasma bubbles is 70% of 980 nm=60 W and 28 W at 1470 nm. Consequently, the plasma bubble is pumped by the two radiations (980+1470 nm), and the residual radiation at 980 nm, can work overlapping the plasma bubble to improve the haemostasis effect. Similarly combinations of (980+1940 nm), or (1470+1940 nm) will also be effective.

Thus, clinical and in vitro tests show that with low power of 1470 nm wavelength, a plasma bubble can be generated, and with the 980 nm wavelength, which has a lower cost and higher efficiency, amplification and growth of this plasma bubble can be achieved.

Additional tests have shown that with the COMBO laser, using 1000 um conical fibers and a power of 120 W, measurements were 35 W at 1470 nm and 93 W at 980 nm.

Figure 3:
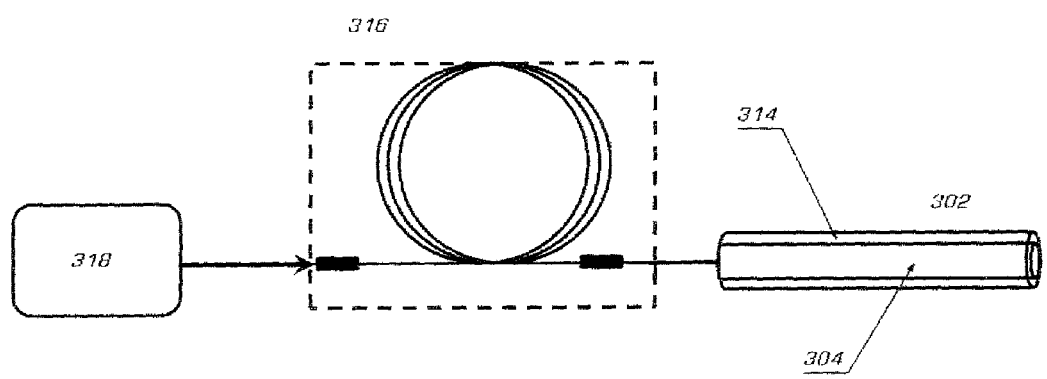
FIG. 3 shows another embodiment of the system of the present invention.

In another preferred embodiment shown in FIG. 3, other combinations of laser sources can be used to achieve diode pumped laser device to generate plasma utilizing plasma ignition means and pulse energizing means. For instance, double core fiber 302 in which the ignition radiation is guided in single mode core/inner core 304 and the radiation used to maintain and enhance the pulse is guided into surrounding second core/outer core 314. The single mode or near single mode radiation comes from fiber laser 316 at 1550+60 nm diode pumped or a q-switched and the fiber elongated pulse of a diode pumped green laser, and radiation for pulse maintenance and enhancement, which is the mayor part of the energy would come from diode laser 318. The 1550 nm pulses can be generated from 915-980 or 1480 laser diode pumps.

Figure 4:
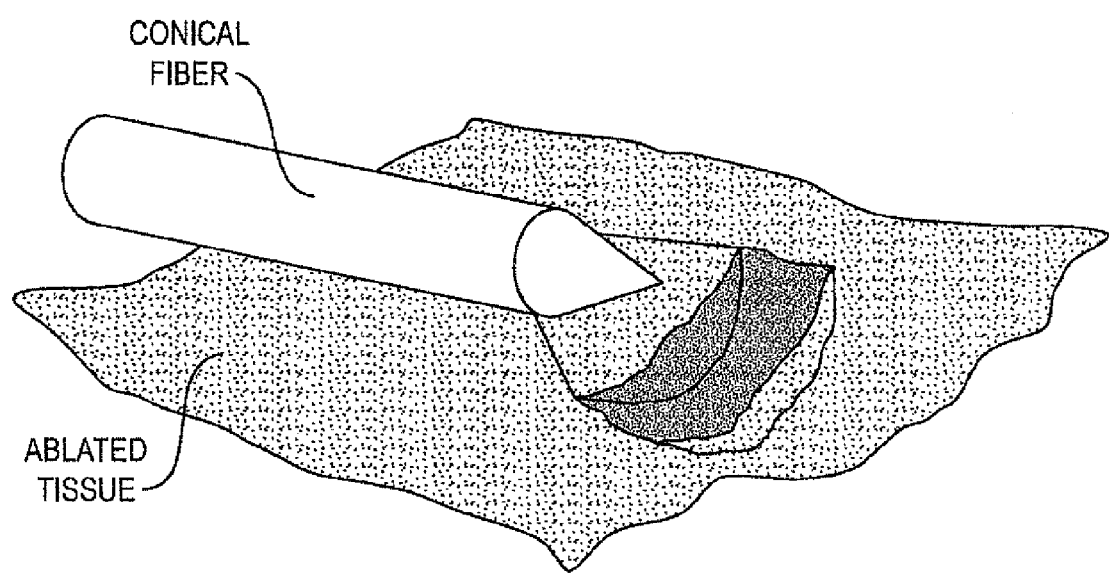
FIG. 4 depicts furrow production on soft tissue by means of laser radiation delivered through a conical tip optical fiber.

After in vitro tests, the excellent efficacy of the double band diode laser is evident, and leads to faster treatments in BPH procedures. The possibility of using an is optical fiber capable of emitting radiation on a larger tissue surface was conceived, in order to obtain more tissue ablation in each sweep. As a consequence, usage of conical fibers with a 1000 μm core diameter was proposed, in order to irradiate larger surfaces on prostatic tissue. So, by using conical fibers instead of side firing fibers allowed using the fast thermo-ablative effects of 1470 nm radiations. After each sweep a large and clean furrow was obtained, without bleeding. Furrow obtained was larger than that produced by side firing fibers, which however produces a deeper coagulation effect. With conical fibers, ablation efficacy was combined with a good hemostasis effect, allowing for a complete BPH treatment faster than other similar laser procedures, and faster even than the traditional TURP treatment. In FIG. 4, conical fiber induced furrow can be observed.

In another preferred embodiment asymmetric off-axis emitting fibers may be employed, such as twister fibers disclosed in U.S. Patent Application 61/245,484 by Neuberger. These fibers allow for better twistability and maneuvering possibilities.

For BPH treatment of prostate with dimension of 50 gr, when using power setting of 100 W and 110 W, total treatment time for the ablation of prostatic adenoma was 18-20 min. It must be considered that the same prostate dimension can be treated with TURP modalities in 25-30 minutes, 20% slower than the treatment with double band diode laser.

Patients in post treatment referred no pain or any other inconvenient. No bleeding was observed and the catheter was removed in the same day.

Having described preferred embodiments of the invention with reference to the accompanying drawings, it is to be understood that the invention is not limited to the precise embodiments, and that various changes and modifications may be effected therein by skilled in the art without departing from the scope or spirit of the invention as defined in the appended claims.

What is claimed is:

1. A medical laser device for enhanced medical treatment comprising:
   at least one laser light source; and
   a transmission medium having a proximal end in optical contact with said at least one light source and a distal end adapted to be positioned near a treatment site;
   wherein said at least one laser light source emits, in substantially continuous mode, a laser light having at least one preselected wavelength that is highly absorbed at said treatment site or its vicinity;
   wherein said at least one laser light source, said transmission medium and said preselected wavelength are selected such that said laser light is delivered to said treatment site in a continuous wave and with a power density sufficient to form a plasma and/or high energy vapor bubble region at said distal end of said transmission medium in close proximity to a tissue treatment site; said plasma and/or high energy vapor bubble region delivering thermal energy to a surrounding medium, causing thermo-ablation.

2. The medical laser device according to claim 1, further including a catheter adapted to enter the urinary tract of a patient.

3. The medical laser device according to claim 1, wherein said transmission medium is at least one optical fiber.

4. The medical laser device according to claim 3, wherein said at least one optical fiber has a double core structure, wherein a laser light having one wavelength travels in an inner core and a laser light having another wavelength is transmitted in an outer core.

5. The medical laser device according to claim 3, wherein one laser light source is a fiber laser and another laser light source is a pump laser for said fiber laser, and wherein laser light from both laser light sources is transmitted by said at least one optical fiber.

6. The medical laser device according to claim 5, wherein said at least one optical fiber has a concentric core structure, wherein said fiber laser wavelength travels in an inner core and a pump laser wavelength is transmitted in an outer core.

7. The medical laser device according to claim 5, wherein said fiber laser emits a laser light having a wavelength of 1550±60 nm, and said pump laser emits a laser light having a wavelength of either 915-980 nm or 1470±60 nm.

8. The medical laser device according to claim 3, wherein said at least one optical fiber is a twister fiber.

9. The medical laser device according to claim 1, wherein said laser light source is a diode laser, operating at wavelengths of either 980±60 nm, 1470±60 nm, or 1940±60 nm.

10. The medical laser device according to claim 9, wherein at least two of the preferred wavelengths are employed in the combination of 980 nm and 1470 nm; 980 nm and 1940 nm or 1470 nm and 1940 nm.

11. The medical laser device according to claim 1, wherein said laser light source is a thulium laser operating in a continuous or semi-continuous mode.

12. The medical laser device according to claim 1, wherein said transmission medium comprises a conical tip at said distal end, said conical tip being configured to focus the laser light and achieve a sufficiently high power density at said distal end of said transmission medium to form a plasma and/or high energy vapor bubble region.

13. A medical treatment utilizing a plasma and/or high energy vapor bubble, comprising:
    transmitting energy generated by a suitably powerful laser light source to a distal end of a transmission medium, which is in the vicinity of a tissue to be treated, to achieve desired medical effects in said tissue such as vaporization, coagulation, ablation, cutting, or other medical effect;
    wherein said laser light source operates in a substantially continuous mode, having at least one preselected wavelength that is highly absorbed at said treatment site;
    delivering said energy to the vicinity of said tissue in a continuous wave and forming a plasma and/or high energy vapor bubble region at said distal end of said transmission medium;
    wherein said laser light source, said transmission medium and said at least one preselected wavelength of emission from said laser light source are selected so that laser light power density is sufficient to form the plasma and/or high energy vapor bubble region at said distal end of said transmission medium;
    delivering thermal energy to a surrounding medium and causing thermo-ablation to said tissue by said plasma and/or high energy vapor bubble region; and
    wherein said tissue contains sufficient quantities of water and/or is in an aqueous environment provided by saline solution, biocompatible liquids, or combination of these.

14. The medical treatment according to claim 13, wherein said laser light source is a diode laser, operating at wavelengths of either 980±60 nm, 1470±60 nm, or 1940±60 nm.

15. The medical treatment according to claim 13, wherein the transmission medium comprises at least one optical fiber having a double core structure, wherein a laser light having one wavelength travels in an inner core and a laser light having another wavelength is transmitted in an outer core.

16. The medical treatment according to claim 15, wherein at least two of the preferred wavelengths are employed in the combination of 980 nm and 1470 nm; 980 nm and 1940 nm, or 1470 nm and 1940 nm.

17. The medical treatment according to claim 15, wherein one laser light source is a fiber laser and another laser light source is a pump laser for said fiber laser, and wherein laser light from both laser light sources is transmitted by said at least one optical fiber.

18. The medical treatment according to claim 17, wherein said at least one optical fiber has a concentric core structure, wherein said fiber laser wavelength travels in an inner core and a pump laser wavelength is transmitted in an outer core.

19. The medical treatment according to claim 18, wherein said fiber laser emits a laser light having a wavelength of at 1550±60 nm, and said pump laser emits a laser light having a wavelength of either 915-980 nm or 1470±60 nm.

20. The medical treatment according to claim 13, wherein said laser light source is a thulium laser operating in a continuous or semi-continuous mode.

* * * * *